United States Patent
Yano et al.

(10) Patent No.: US 8,277,920 B2
(45) Date of Patent: Oct. 2, 2012

(54) OPTICAL RECORDING MATERIAL, CHALCONE TYPE COMPOUNDS AND METAL COMPLEXES

(75) Inventors: Toru Yano, Tokyo (JP); Yohei Aoyama, Tokyo (JP)

(73) Assignee: Adeka Corporation, Tokyo (JP)

( * ) Notice: Subject to any disclaimer, the term of this patent is extended or adjusted under 35 U.S.C. 154(b) by 984 days.

(21) Appl. No.: 12/296,594

(22) PCT Filed: Apr. 24, 2007

(86) PCT No.: PCT/JP2007/058801
§ 371 (c)(1),
(2), (4) Date: Oct. 9, 2008

(87) PCT Pub. No.: WO2007/125892
PCT Pub. Date: Nov. 8, 2007

(65) Prior Publication Data
US 2009/0269541 A1    Oct. 29, 2009

(30) Foreign Application Priority Data
Apr. 28, 2006    (JP) .................................. 2006-127030

(51) Int. Cl.
B32B 3/02    (2006.01)
G11B 7/24    (2006.01)

(52) U.S. Cl. ...... 428/64.8; 428/64.4; 548/402; 548/403; 548/427; 548/468; 430/270.16; 430/270.18; G9B/7.15; G9B/7.156

(58) Field of Classification Search ............... 428/64.4, 428/64.8; 430/270.16, 270.18, 270.2, 270.21; 548/402, 403, 427, 468; G9B/7.15, 7.151, G9B/7.156, 7.158
See application file for complete search history.

(56) References Cited

U.S. PATENT DOCUMENTS

| | | | |
|---|---|---|---|
| 4,210,591 A * | 7/1980 | Burri | 548/409 |
| 5,141,841 A * | 8/1992 | Wade | 430/281.1 |
| 5,519,136 A * | 5/1996 | Wade | 546/174 |
| 2003/0103443 A1 | 6/2003 | Ishida et al. | |
| 2006/0019198 A1 | 1/2006 | Yeh et al. | |

FOREIGN PATENT DOCUMENTS

| | | |
|---|---|---|
| CN | 1423263 | 6/2003 |
| EP | 0 135 348 | 3/1985 |
| JP | 2003-165272 | 6/2003 |
| JP | 2004-306306 | 11/2004 |
| TW | 200605062 | 2/2006 |

OTHER PUBLICATIONS

Petillon et al.(Rev.Chim.Miner. 1973, 10(5), p. 723-732.*
SciFinder Abstract of Kiremire reference prepared on Jan. 4, 2012.*
Kiremire et al. "The Synthesis and characterization of a novel high spin charge transfer iron (III) complex containing imidazoline nitroxyl free radical ligand", Orient. J. Chem., 2004, 20, p. 13-16.*
Chinese Patent Office issued a Chinese Office Action dated Feb. 12, 2010, Application No. 200780012800.
European Search Report—EP 07 74 2236—Oct. 15, 2010.
Japanese Notice of Rejection—2008-513205—Mar. 21, 2012.
Taiwanese Office Action dated May 25, 2012 with English translation; Application No. 096114600.
JP Notice of Rejection dated Jun. 26, 2012 with English translation; Application No. 2008-513205.
N.M. Przhiyalgovskaya et al., Acetylenic Fragmentation of Acylated Derivatives of Fischer's Base, 1987 (7), p. 915-918.

* cited by examiner

*Primary Examiner* — Gerard Higgins
(74) *Attorney, Agent, or Firm* — Young & Thompson

(57) ABSTRACT

An optical recording material comprising at least one kind of chalcone type compound represented by the following general formula (I) or a metal complex using the chalcone type compound as a ligand:

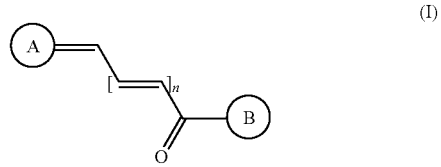

wherein ring A represents a 5- or 6-membered heterocyclic ring or an aromatic ring; ring B represents a 5- or 6-membered heterocyclic ring, an aromatic ring, or a metallocene structure; the above-mentioned heterocyclic and aromatic ring may be condensed with other rings or may be substituted; n is 0 or 1.

13 Claims, No Drawings

OPTICAL RECORDING MATERIAL, CHALCONE TYPE COMPOUNDS AND METAL COMPLEXES

TECHNICAL FIELD

The present invention relates to an optical recording material used for an optical recording medium, in which information provided as information patterns by means of a laser and the like is recorded. More particularly, the present invention relates to an optical recording material used for an optical recording medium which is capable of high-density optical recording and reproduction by a laser of a wavelength in ultraviolet and visible regions, and of low energy, and the like, and also relates to a novel chalcone type compound and a novel metal complex comprising the compound as a ligand suitable for the optical recording material.

BACKGROUND ART

The optical recording media are in widespread use, generally due to its superior characteristics such as large recording capacities, non-contact recording or reproduction, and the like. In the write-once optical discs such as WORM, CD-R, DVD±R, and the like, recording is carried out by focusing the laser light on a minute area of the recording layer to change properties of the optical recording layer, while reproduction is performed based on a difference in intensities of light reflected from the recorded area and non-recorded area.

Presently, in the optical discs mentioned above, the wavelength of a semiconductor laser used for recording and reproduction is between 750 and 830 nm for CD-R and between 620 and 690 nm for DVD-R. However, in order to realize further increase in capacity, an optical disc which uses short-wavelength laser light is being explored. For example, one which uses light of wavelength between 380 and 420 nm as the recording light is under study.

In an optical recording medium for the short-wavelength recording light, various compounds are used to form the optical recording layer. For example, Patent Document 1 reports an optical information recording medium comprising a metal complex containing a chalcone type compound as a ligand and Patent Document 2 reports an optical recording medium comprising a specific chalcone type compound. However, these compounds used for an optical recording medium did not necessarily have absorption wavelength characteristics suitable for an optical recording material used to form an optical recording layer.

Further, Patent Document 3 reports a light absorber for clothing material and, as an example of a compound used suitably as the light absorber, an organic dye compound having a chalcone type structure is cited. However, there is no description nor suggestion that the organic dye compound having the chalcone type structure may be used as an optical recording material.

Patent Document No. 1: Japanese Patent Laid-Open Publication No. 2003-11511
Patent Document No. 2: Japanese Patent Laid-Open Publication No. 2004-306306
Patent Document No. 3: Japanese Patent Laid-Open Publication No. 2000-328039

DISCLOSURE OF THE INVENTION

Problems to be Solved by the Invention

Accordingly, an object of the present invention is to provide an optical recording material suitable for forming an optical recording layer of an optical recording medium for short-wavelength recording light and to provide a novel compound suitable for the optical recording material.

Means for Solving the Problems

The present inventors conducted diligent research and, as a result, found that a specific chalcone type compound and a metal complex comprising the chalcone type compound as a ligand are suitable for forming an optical recording layer of an optical recording medium which is recorded or reproduced by short-wavelength recording light, especially laser light of wavelength between 320 and 420 nm.

The present invention has been made based on the above findings and accomplished the above-mentioned objects by providing an optical recording material comprising at least one kind of chalcone type compound represented by the following general formula (I):

[Formula 1]

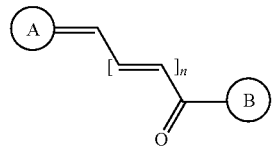

wherein n is 0 or 1; rings A and B represent each independently a 5- or 6-membered heterocyclic ring, an aromatic ring, or a metallocene structure; the heterocyclic and aromatic rings may be condensed with other rings or may be substituted.

In addition, the present invention has accomplished the above-mentioned objects by providing an optical recording material comprising a metal complex using the chalcone type compound represented by the general formula (I) as a ligand.

Further, the present invention has accomplished the above-mentioned objects by providing an optical recording medium characterized by an optical recording layer disposed on a substrate, the recording layer formed of the optical recording material.

Furthermore, the present invention provides a chalcone type compound represented by the following general formula (III) which is suitable as the optical recording material.

Also, the present invention provides a metal complex represented by the following general formula (VI) which is suitable as the optical recording material.

BEST MODE FOR CARRYING OUT THE INVENTION

Hereafter, the optical recording material of the present invention comprising at least one kind of chalcone type compound represented by the general formula (I), the optical recording material of the invention comprising a metal complex using the chalcone type compound as a ligand (hereafter, these two recording materials may together be referred to as the optical recording material of the present invention), an optical recording medium of the invention, a novel chalcone type compound of the invention, and a novel metal complex of the invention will be described in detail based on preferable embodiments. It is noted that, with the chalcone type compound and the metal complex containing the same as a ligand, both according to the present invention, there are cases where optical isomers such as enantiomers, diastereomers, or a racemic mixture are present. In such a case, any optical isomer among these may be isolated and used as such or may be used as a mixture thereof in the optical recording material of the invention. Hereafter, unless otherwise noted, optical isomers will not be differentiated in the present invention.

First, the chalcone type compound represented by the general formula (I) will be described.

In the general formula (I), the 5-membered heterocyclic ring represented by rings A and B includes, for example, a pyrrole, pyrazolidine, pyrazole, imidazole, imidazolidine, oxazole, isoxazole, isoxazolidine, thiazole, isothiazolidine rings, and the like; the 6-membered heterocyclic ring represented by rings A and B includes, for example, a piperidine, piperazine, morpholine, thiomorpholine, julolidine, pyridine, pyrazine, pyrimidine, pyridazine, triazine rings, and the like. The 5- or 6-membered heterocyclic ring and an aromatic ring represented by rings A and B may be condensed with other rings or may be substituted, with examples including a quinoline, isoquinoline, indole, julolidine, naphthalene, anthracene, phenanthrene, phenylbenzene rings, and the like.

In addition, the metallocene structure represented by ring B includes a ferrocenyl, nickelocenyl, cobaltocenyl structures, and the like. When ring B is of a metallocene structure, a carbonyl group is bonded to one of the cyclopentadiene rings of the metallocene.

Among the chalcone type compounds represented by the general formula (I), those having a structure represented by the following general formula (II) are preferable because they have more adequate light absorption characteristics as an optical recording material:

[Formula 2]

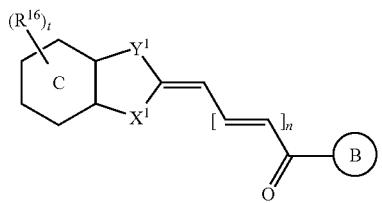

(II)

wherein ring B and n are the same as in the general formula (I); ring C represents a benzene or naphthalene ring; $R^{16}$ may be the same or different and represents an alkyl group having 1 to 8 carbon atoms which may be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms; $X^1$ represents an oxygen atom, a sulfur atom, or N—$R^d$; $Y^1$ represents NH or C—$R^e(R^f)$; $R^d$, $R^e$, and $R^f$ each independently represent a hydrogen atom, an alkyl group having 1 to 8 carbon atoms, an alkenyl group having 2 to 8 carbon atoms, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms; t represents an integer from 0 to 6; each of the above-mentioned alkyl group having 1 to 8 carbon atoms, an aryl group having 6 to 30 carbon atoms, an arylalkyl group having 7 to 30 carbon atoms, a metallocenyl group having 10 to 30 carbon atoms, a heterocyclic ring group having 2 to 30 carbon atoms may have a substituent.

In addition, among the chalcone type compounds represented by the general formula (I), those having a structure represented by the following general formula (III) are preferable because they are chemically and thermally stable and can be manufactured economically:

[Formula 3]

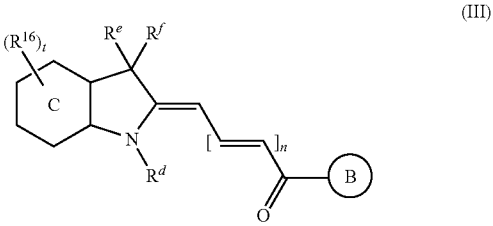

(III)

wherein ring B, ring C, $R^{16}$, $R^d$, $R^e$, $R^f$, t, and n are the same as in the general formula (II).

Further, among the chalcone type compounds represented by the general formula (I), those having a structure represented by the following general formula (IV) are useful because they can coordinate easily with metals:

[Formula 4]

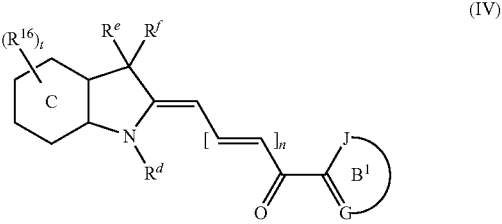

(IV)

wherein ring C, $R^{16}$, $R^d$, $R^e$, $R^f$, t, and n are the same as in the general formula (II); ring $B^1$ is a 5- or 6-membered ring; G represents CH or a nitrogen atom; J represents an oxygen or sulfur atom, CH, or $CH_2$.

Furthermore, among the chalcone type compounds represented by the general formula (I), those having a structure represented by the following general formula (V) are useful because they can coordinate easily with metals and, by coordinating with metals, they can acquire more adequate light absorption characteristics as an optical recording material:

[Formula 5]

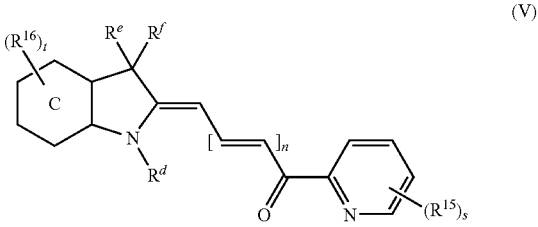

(V)

wherein ring C, $R^{16}$, $R^d$, $R^e$, $R^f$, t, and n are the same as in the general formula (II); $R^{15}$ may be the same or different and represents an alkyl group having 1 to 8 carbon atoms which may be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms; each of the above-mentioned alkyl group having 1 to 8 carbon atoms, aryl group having 6 to 30 carbon atoms, arylalkyl group having 7 to 30 carbon atoms, metallocenyl group having 10 to 30 carbon atoms, and heterocyclic group having 2 to 30 carbon atoms may have a substituent; s represents an integer from 0 to 4.

Next, the structures of the chalcone type compounds represented by the general formulae (II) to (V) will be described.

In the general formula (II), $R^{16}$ represents an alkyl group having 1 to 8 carbon atoms which may be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms. The alkyl group having 1 to 8 carbon atoms includes, for example, methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, 3-cyclohexylpropyl, 4-cyclohexylbutyl, heptyl, isoheptyl, tert-heptyl, n-octyl, isooctyl, tert-octyl, 2-ethylhexyl, norbornyl, and the like, the aryl group having 6 to 30 carbon atoms includes, for example, phenyl, naphthyl, anthracen-1-yl, phenthren-1-yl, tetracenyl, pentacenyl, crycenyl, triphenylenyl, pyrenyl, picenyl, perilenyl, and the like; the arylalkyl group having 7 to 30 carbon atoms includes, for example, benzyl, phenethyl, 2-phenylpropyl, diphenylmethyl, triphenylmethyl, styryl, cinnamyl, and the like; the metallocenyl group having 10 to 30 carbon atoms includes, for example, ferrocenyl, nickelocenyl, cobaltocenyl, and the like; the heterocyclic group having 2 to 30 carbon atoms includes, for example, pyridyl, pyrimidyl, pyridazyl, piperazyl, piperidyl, pyranyl, pyrazolyl, triazyl, pyrrolidyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, julolidyl, morpholinyl, thiomorpholinyl, 2-pyrrolidinon-1-yl, 2-piperidon-1-yl, 2,4-dioxyimidazolidin-3-yl, 2,4-dioxyoxazolidin-3-yl, and the like; the halogen atom includes fluorine, chlorine, bromine, iodine, and the like. In addition, each of the above-mentioned groups including the alkyl group having 1 to 8 carbon atoms, aryl group having 6 to 30 carbon atoms, arylalkyl group having 7 to 30 carbon atoms, metallocene group having 10 to 30 carbon atoms, and heterocyclic group having 2 to 30 carbon atoms may have a substituent. The substituent includes the following with a note that the total number of carbon atoms possessed by $R^{16}$ satisfies the ranges specified above. The substituent includes, for example, an alkyl group such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, decyl, and the like; an alkoxy group such as methoxy, ethoxy, propoxy, isopropoxy, butoxy, sec-butoxy, tert-butoxy, isobutoxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, decyloxy, and the like; an alkylthio group such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, 2-ethylhexylthio, and the like; an alkenyl group such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicocenyl, tricocenyl, and the like; an arylalkyl group such as benzyl, phenethyl, diphenylmethyl, triphenylmethyl, styryl, cinnamyl, and the like; an aryl group such as phenyl, naphthyl, and the like; an aryloxy group such as phenoxy, naphthyloxy, and the like; an arylthio group such as phenylthio, naphthylthio, and the like; a heterocyclic group such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, 2,4-dioxyoxazolidin-3-yl, and the like; a halogen atom such as fluorine, chlorine, bromine, iodine, and the like; an acyl group such as acetyl, 2-chloroacetyl, propionyl, octanoyl, acryloyl, methacryloyl, phenylcarbonyl (benzoyl), phthaloyl, 4-trifluoromethylbenzoyl, pivaloyl, saliciloyl, oxaloyl, stearoyl, methoxycarbonyl, ethoxycarbonyl, tert-butoxycarbonyl, n-octadecyloxycarbonyl, carbamoyl, and the like; an acyloxy group such as acetyloxy, benzoyloxy, and the like; a substituted amino group such as amino, ethylamino, dimethylamino, diethylamino, butylamino, cyclopentylamino, 2-ethylhexylamino, dodecylamino, anilino, chlorophenylamino, toluidino, anicidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, tert-butoxycarbonylamino, n-octadecyloxycarbonylamino, N-methylmethoxycarbonylamino, phenoxycarbonylamino, sulfamoylamino, N,N-dimethylaminosulfonyamino, methylsulfonylamino, butylsulfonylamino, phenylsulfonylamino, and the like; a sulfonamide, sulfonyl, carboxyl, cyano, sulfo, hydroxyl, nitro, mercapto, imide, carbamoyl, sulfonamide groups, and the like. These groups may be further substituted. In addition, the carboxyl and sulfo groups may be in the form of salts.

In the general formula (II), $X^1$ is an oxygen atom, a sulfur atom, or a group represented by N—$R^d$; $Y^1$ is NH or a group represented by C—$R^e(R^f)$; $R^d$, $R^e$, and $R^f$ represent a hydrogen atom, an alkyl group having 1 to 8 carbon atoms, an alkenyl group having 2 to 8 carbon atoms, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group containing 2 to 30 carbon atoms.

The groups represented by $R^d$, $R^e$, and $R^f$, namely an alkyl group having 1 to 8 carbon atoms, an aryl group having 6 to 30 carbon atoms, an arylalkyl group having 7 to 30 carbon atoms, a metallocenyl group having 10 to 30 carbon atoms, a heterocyclic group containing 2 to 30 carbon atoms, and a halogen atom, include those exemplified in the description of $R^{16}$. The alkenyl group having 2 to 8 carbon atoms includes, for example, vinyl, allyl, crotyl, dimethylallyl, 2-pentenyl, 2-hexenyl, 2-heptenyl, 2-octenyl, and the like. In addition, each of the above-mentioned groups including the alkyl group having 1 to 8 carbon atoms, aryl group having 6 to 30 carbon atoms, arylalkyl group having 7 to 30 carbon atoms, metallocenyl group having 10 to 30 carbon atoms, and heterocyclic group having 2 to 30 carbon atoms may have a substituent as with $R^{16}$. The substituent includes the groups exemplified in the description of $R^6$. When $R^d$, $R^e$, and $R^f$ have substituents, the total number of carbon atoms satisfies the ranges specified above.

In the general formula (IV), the ring $B^1$ is a 5- or 6-membered ring, wherein the ring may be comprised of all carbon atoms or may be a heterocyclic ring. The ring comprised of all carbon atoms includes a cyclopentadiene or benzene ring; the 5-membered heterocyclic ring includes, for example, a furan, thiophene, pyrrole, pyrazolidine, pyrazole, imidazole, imidazolidine, oxazole, isoxazole, isoxazolidine, thiazole, isothiazolidine rings, and the like; the 6-membered heterocyclic ring includes a piperidine, piperazine, morpholine, thiomorpholine, pyridine, pyrazine, pyrimidine, pyridazine, triazine, quinoline, isoquinoline, julolidine rings, and the like.

In the general formula (V), $R^{15}$ represents an alkyl group having 1 to 8 carbon atoms which may be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms. The alkyl group having 1 to 8 carbon atoms, aryl group having 6 to 30 carbon atoms, arylalkyl group having 7 to 30 carbon atoms, metallocenyl group having 10 to 30 carbon atoms, and heterocyclic group containing 2 to 30 carbon atoms include the groups exemplified in the description of $R^{16}$. Each of these groups may be substituted and, as the substituent, those exemplified in the description of $R^{16}$ may be cited. When $R^{15}$ has a substituent, the total number of carbon atoms satisfies the ranges specified above.

The specific examples of the chalcone type compound of the present invention, represented by the general formulae (I) to (V), include the following compound Nos. 1 to 42:

[Formula 6]

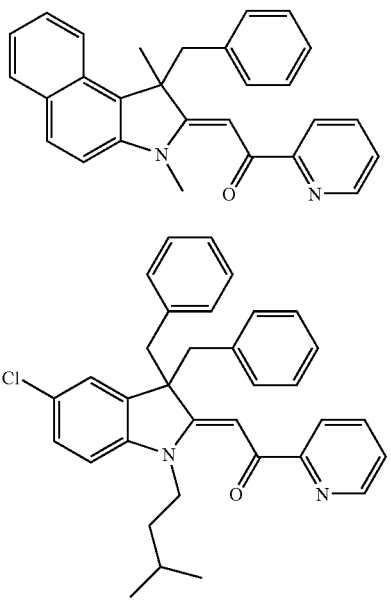

Compound No. 1

Compound No. 2

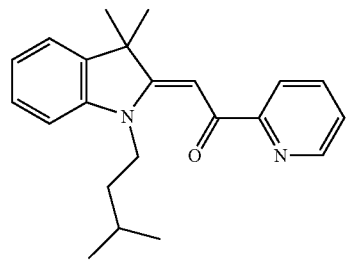

Compound No. 3

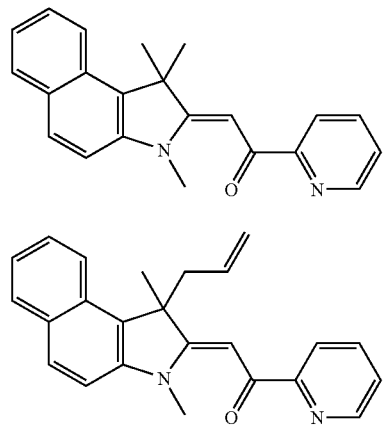

Compound No. 4

Compound No. 5

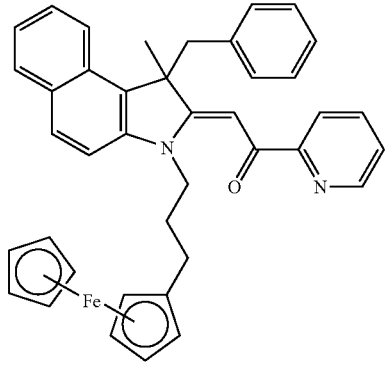

Compound No. 6

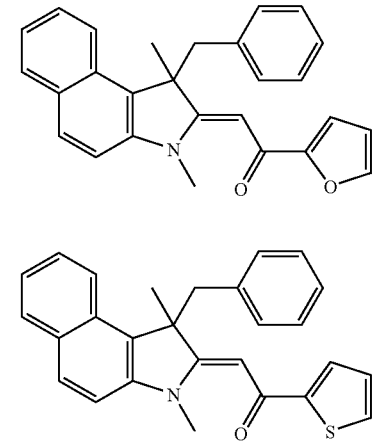

Compound No. 7

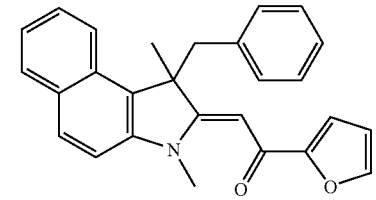

Compound No. 8

Compound No. 9
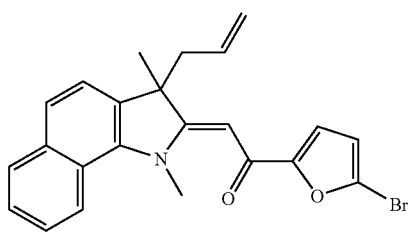
Compound No. 10
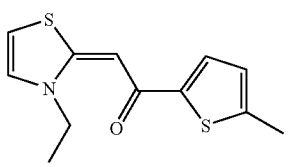
Compound No. 11
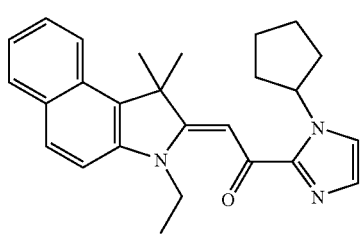
Compound No. 12
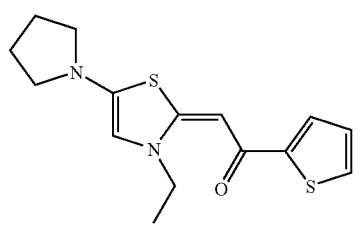
Compound No. 13
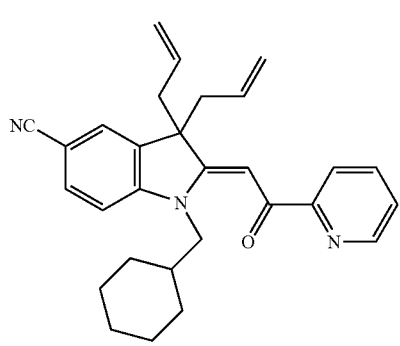
Compound No. 14
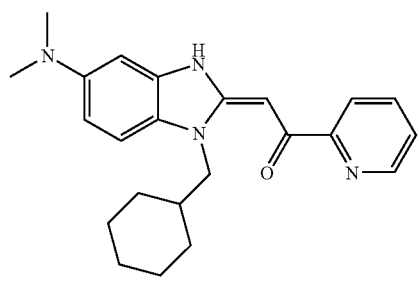
Compound No. 15
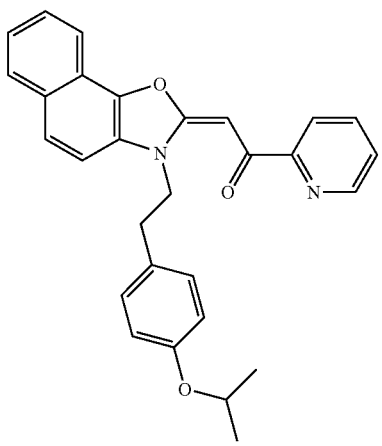
Compound No. 16
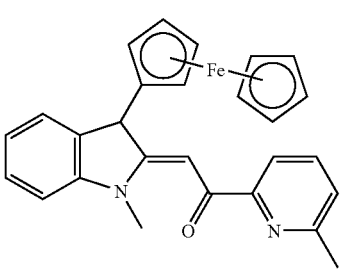
Compound No. 17
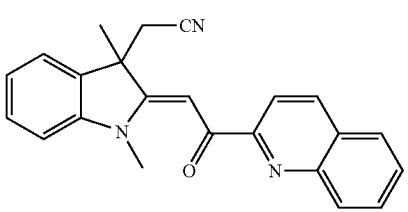
Compound No. 18
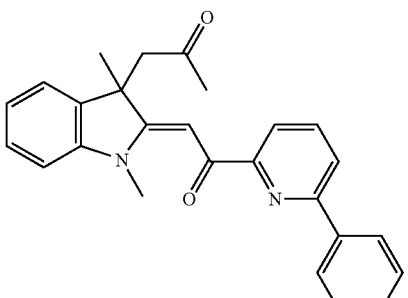
Compound No. 19
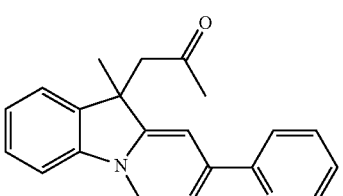

[Formula 7]
Compound No. 20
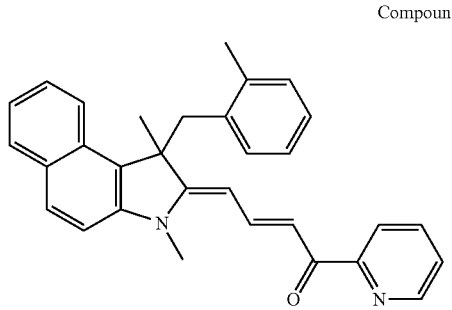
Compound No. 21
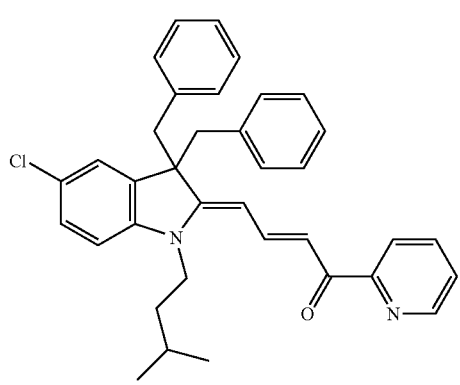
Compound No. 22
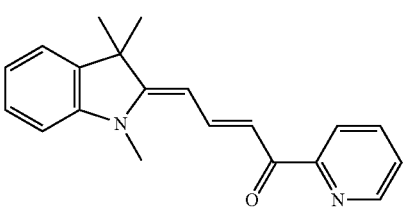
Compound No. 23
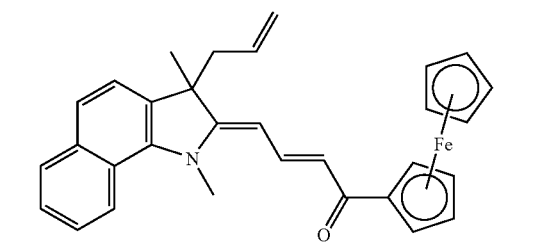
Compound No. 24
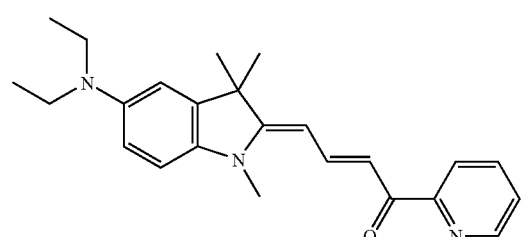
Compound No. 25
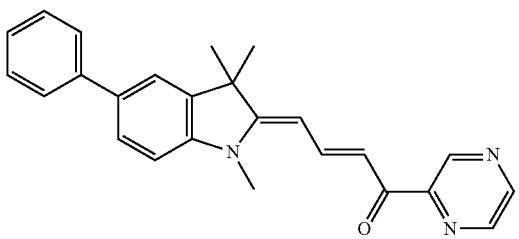
Compound No. 26
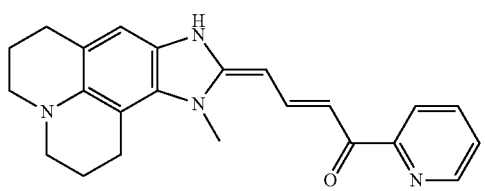
[Formula 8]
Compound No. 27
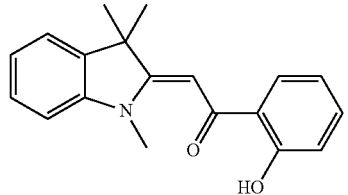
Compound No. 28
Compound No. 29
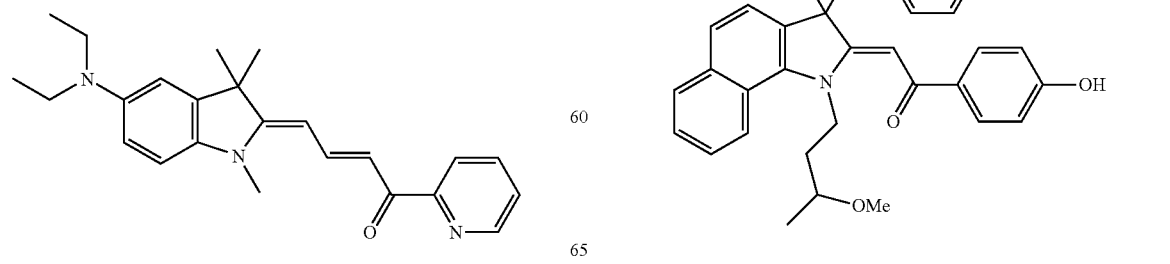

Compound No. 30
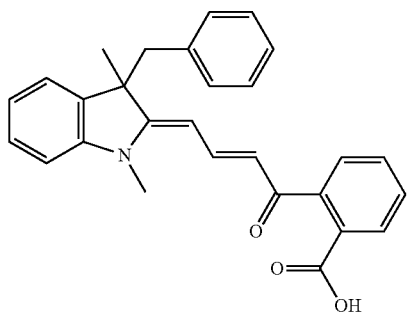
Compound No. 31
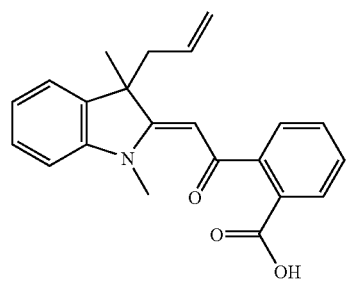
Compound No. 32
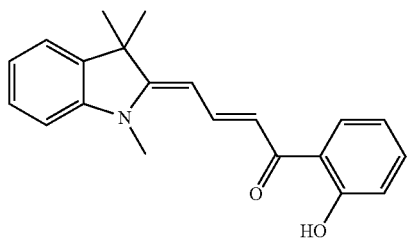
Compound No. 33
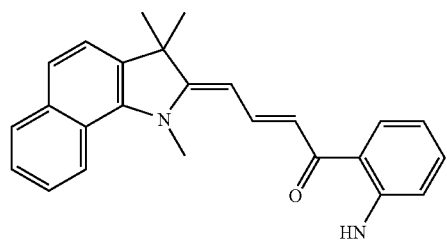
Compound No. 34
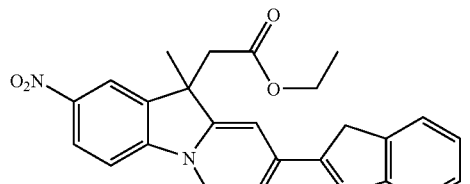
Compound No. 35
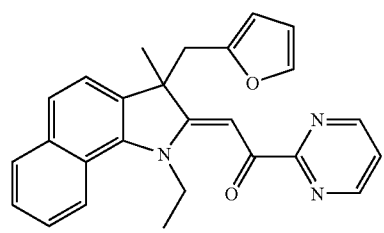
Compound No. 36
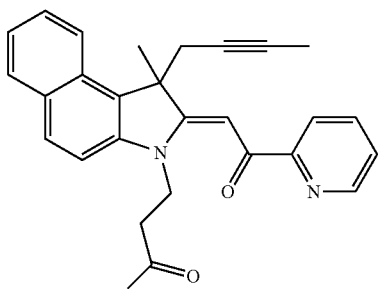
Compound No. 37
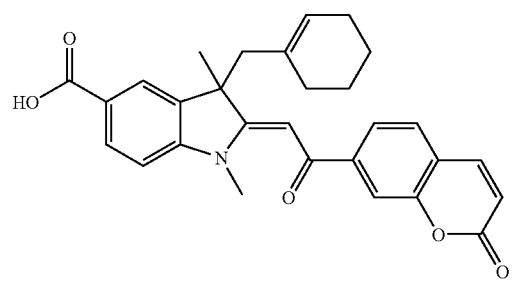
Compound No. 38
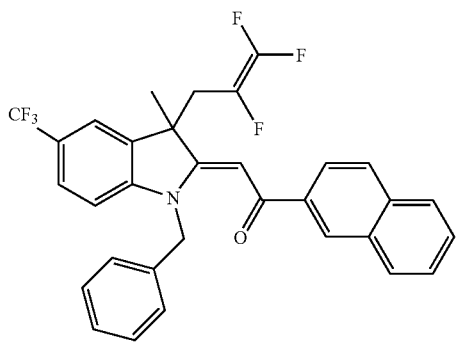
Compound No. 39
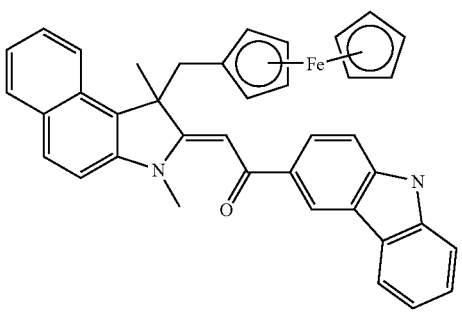
Compound No. 40
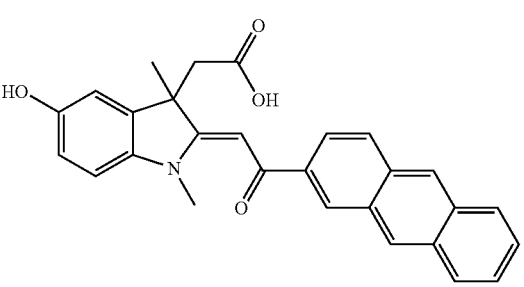

-continued

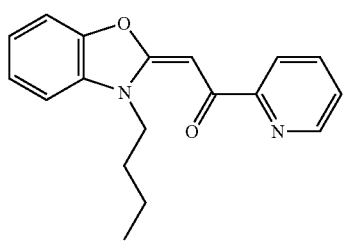
Compound No. 41

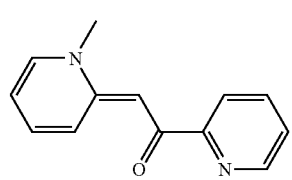
Compound No. 42

There is no particular restriction on the method of manufacture of any of the chalcone type compounds represented by the general formula (I) and they can be obtained by methods using publicly known reactions. As the method of manufacture, for example when n is 0, there may be mentioned a synthetic method according to the route shown in the following [Formula 9], where a corresponding active methylene compound is reacted with a corresponding acid chloride compound:

[Formula 9]

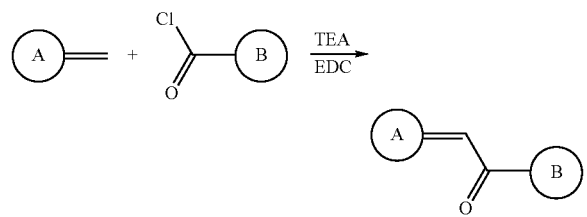

wherein rings A and B each independently represent a 5- or 6-membered heterocyclic ring, an aromatic ring, or a metallocene structure; the heterocyclic and aromatic rings may be condensed with other rings or may be substituted.

Further, when n is 1, there may be mentioned a synthetic method according to the route shown in the following [Formula 10], where a corresponding aldehyde compound or formamide derivative is reacted with a corresponding ketone compound:

[Formula 10]

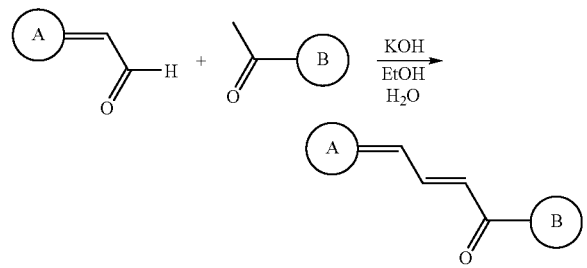

wherein rings A and B each independently represent a 5- or 6-membered heterocyclic ring, an aromatic ring, or a metallocene structure; the heterocyclic and aromatic rings may be condensed with other rings or may be substituted.

Among the chalcone type compounds represented by the general formula (I), those represented by the general formula (II) are preferable as the optical recording material of the present invention; among the chalcone type compounds represented by the general formula (II), those represented by the general formula (III) are more preferable; among the compounds represented by the general formula (III), those represented by the general formula (IV) are even more preferable; among the compounds represented by the general formula (IV), those represented by the general formula (V) are the most preferable. Among these chalcone type compounds, those represented by the general formulae (III) to (V) are new compounds and include the above-mentioned compound Nos. 1 to 9, No. 11, No. 13, Nos. 16 to 25, and Nos. 27 to 40.

Next, the optical recording material of the present invention, comprising a metal complex using the above-mentioned chalcone type compound as a ligand, will be described.

The metal complex is formed with any of the chalcone type compounds represented by the general formulae (I) to (V) used as a ligand. The metal complex refers to a compound where at least one of the coordinating sites of the compounds represented by the general formulae (I) to (V) coordinates to a metal atom, more specifically a compound where the oxygen atom of the carbonyl group of the compounds represented by the general formula (I) to (V) and the metal binding atom contained in rings A and/or B bonds to the metal atom to form at least one chelate stricture. It is also possible that each of the two coordinating sites possessed by the ligand is bonded to different metals.

An optical recording layer, comprising the metal complex in which the chalcone type compound described above is coordinated, has a merit that the light resistance of the optical recording layer is improved. Therefore, as an optical recording material, it is preferable to utilize the metal complex comprising the chalcone type compound as a ligand. Among these metal complexes, the novel metal complex represented by the following general formula (VI), in which the chalcone type compound represented by the general formula (V) is coordinated, is preferable because it has light absorption characteristics adequate for an optical recording material.

[Formula 11]

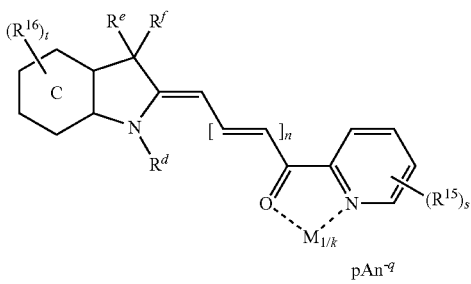

wherein ring C, $R^{16}$, $R^d$, $R^e$, $R^f$, t, and n are the same as in the general formula (II); $R^{15}$ and s are the same as in the general formula (V); M represents a metal atom selected from a group consisting of elements of the periodic table Groups 2, 8, 9, 10, 11, 12, and 13; $M_{1/k}$ represents a structure where k ligands of the same kind coordinate to metal M; k is an integer from 2 to 4; $An^{q-}$ represents a q-valent anion; q is 1 or 2; p represents a coefficient to keep the charge neutral.

In the general formula (VI), the metal atom represented by M is preferably copper, nickel, cobalt, iron, or aluminum, because the complexes comprising these metals can be manufactured economically and show excellent light absorption characteristics.

In the general formula (VI), the anion represented by $An^{q-}$ includes, as a monovalent anion, for example, a halide ion such as a chloride, bromide, iodide, fluoride anions, and the like; an inorganic anion such as a perchlorate, chlorate, thiocyanate, hexafluorophosphate, hexafluoroantimonate, tetrafluoroborate anions, and the like; an organic sulfonate anions such as a benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate, and a sulfonate anion described in Japanese Patent Laid-Open Publication No. 2004-53799, and the like; an organic phosphate anions such as an octyl phosphate, dodecyl phosphate, octadecyl phosphate, phenyl phosphate, nonylphenyl phosphate, 2,2'-methylenebis(4,6-di-tert-butylphenyl) phosphonate anions, and the like; a bistrifluoromethylsulfonylimide anion; a bisperfluorobutanesulfonylimide anion; a perfluoro-4-ethylcyclohexanesulfonate anion; a tetrakis(pentafluorophenyl)borate anion; and the like. As a divalent anion, for example, a benzenedisulfonate anion, a naphthalenedisulfonate anion, and the like may be cited. There may also be used, as necessary, a quencher anion which can deactivate (quench) the active molecules in the exited state and anions of metallocene compounds such as ferrocene, ruthenocene, and the like, which have an anionic group such as a carboxyl, phosphonate, and sulfonate groups on the cyclopentadienyl ring.

The above-mentioned quencher anion includes, for example, those represented by the following general formula (A) or (B), or formula (C) or (D), or anions described in Japanese Patent Laid-Open Publication Nos. S60-234892, H5-43814, H5-305770, H6-239028, H9-309886, H9-323478, H10-45767, H11-208118, 2000-168237, 2002-201373, 2002-206061, and 2005-297407; Japanese Patent Application Publication No. 17-96334; International Publication No. WO/98/29257, and the like:

[Formula 12]

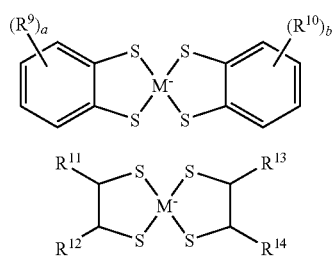

wherein M is the same as in the general formula (VI); $R^9$ and $R^{10}$ represent a halogen atom, an alkyl group having 1 to 8 carbon atoms, an aryl group having 6 to 30 carbon atoms, or a —$SO_2$-G group, G represents an alkyl, aryl that may be substituted with a halogen atom, dialkylamino, diarylamino, piperidino, or morpholino groups; a and b each independently represent an integer from 0 to 4; $R^{11}$, $R^{12}$, $R^{13}$, and $R^{14}$ each independently represent an alkyl, alkylphenyl, alkoxyphenyl, or halogenated phenyl groups:

[Formula 13]

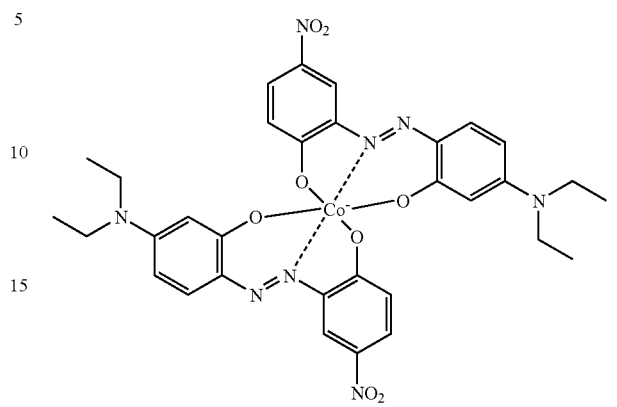

[Formula 14]

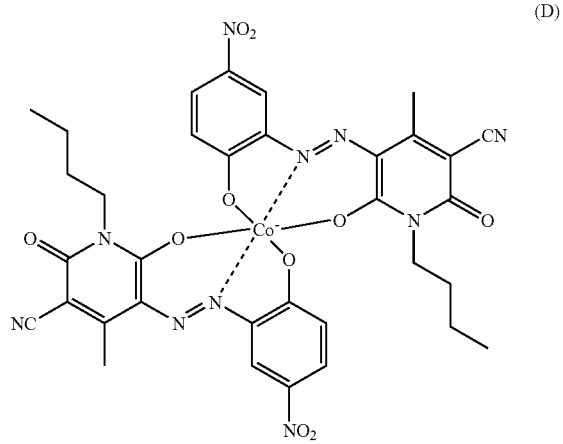

The specific examples of the compound represented by the general formula (VI) of the present invention include the following compound Nos. 43 to 58:

[Formula 15]

Compound No. 43

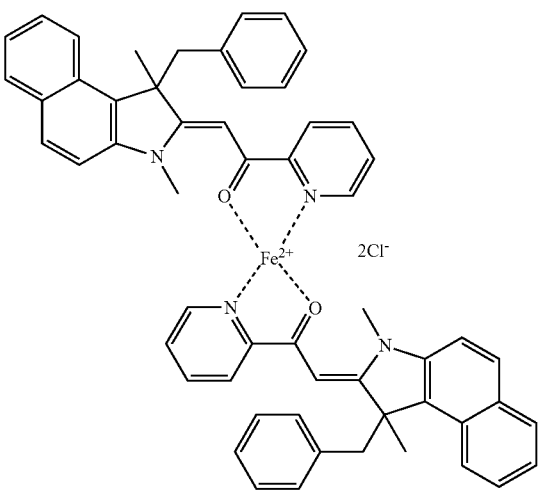

Compound No. 44
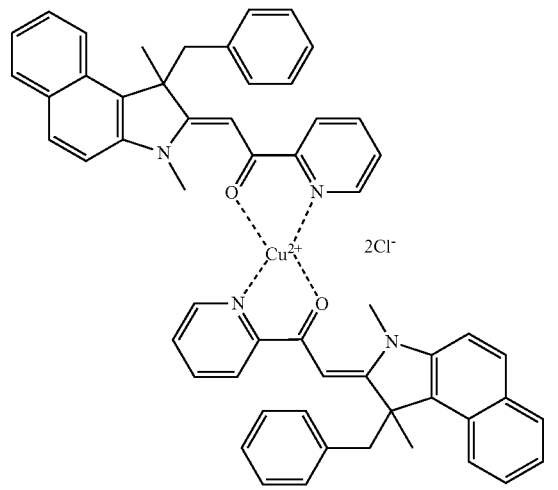
Compound No. 47
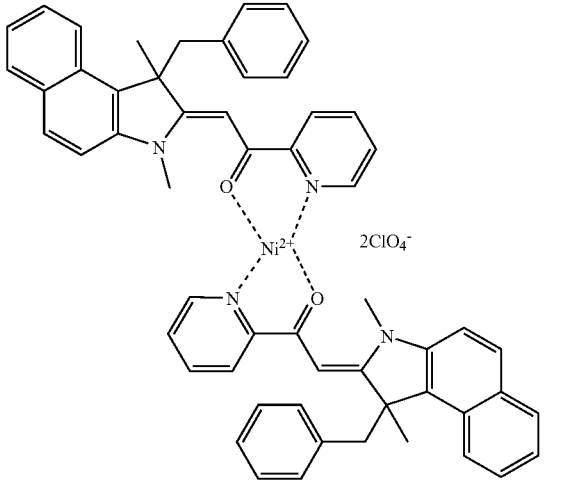
Compound No. 45
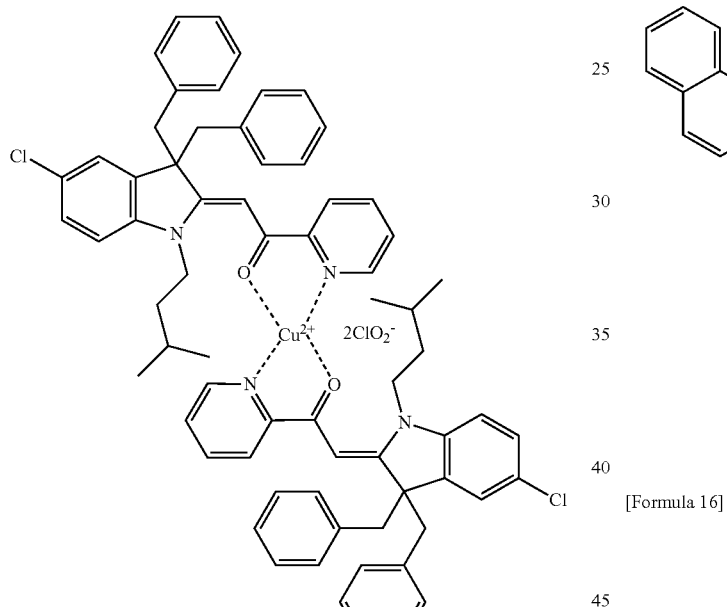
Compound No. 48
Compound No. 49
[Formula 16]
Compound No. 46
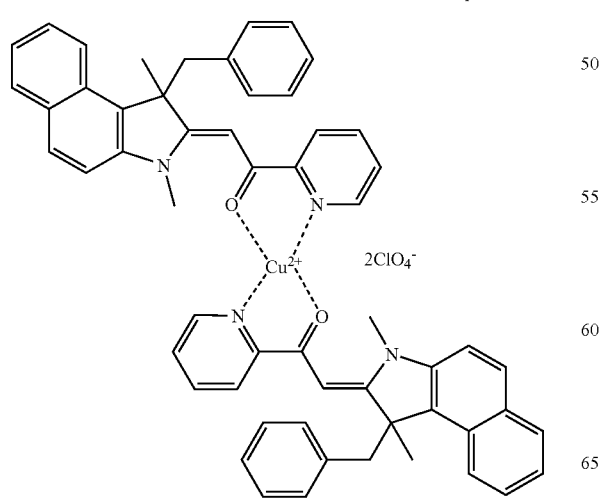
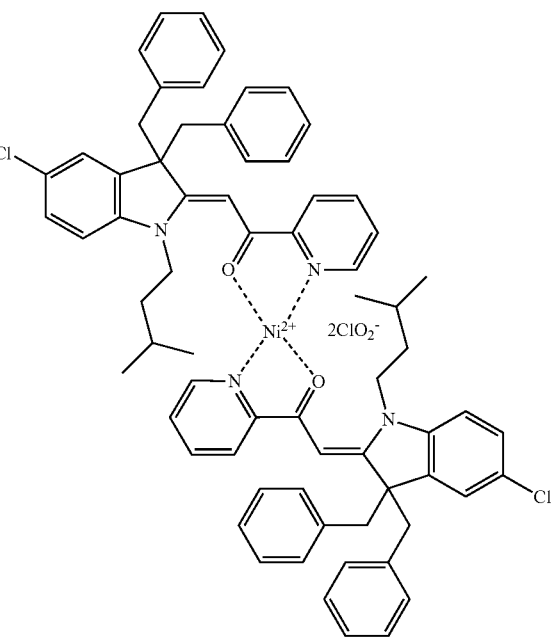

Compound No. 50
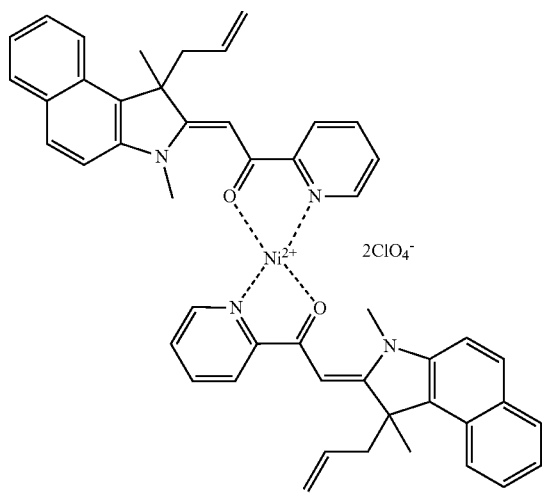
Compound No. 53
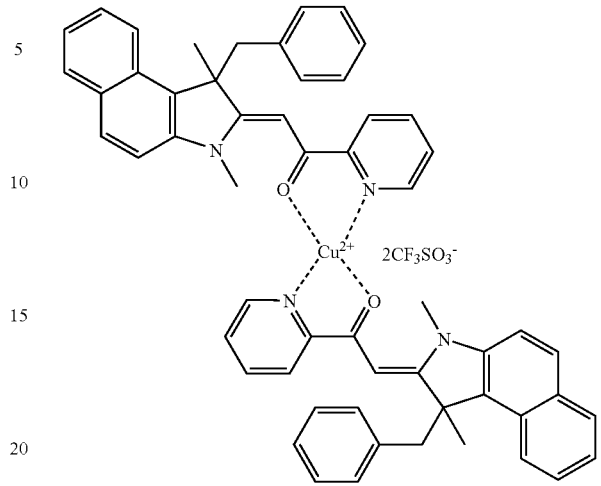
Compound No. 51
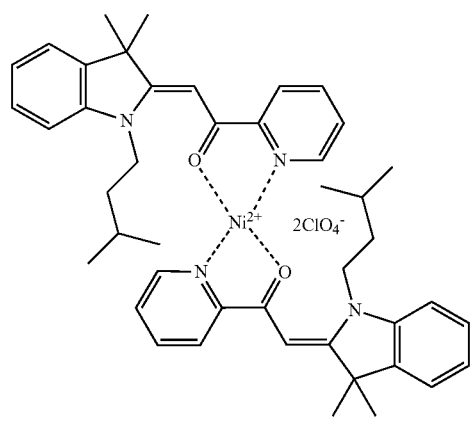
Compound No. 54
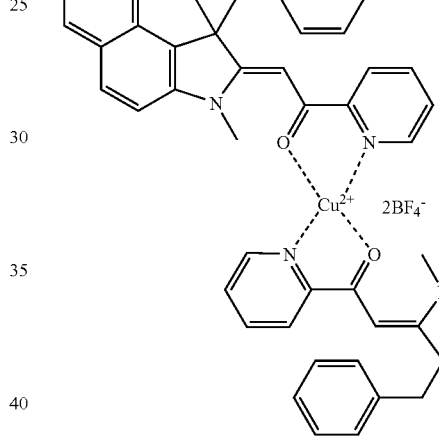
[Formula 17]
Compound No. 52
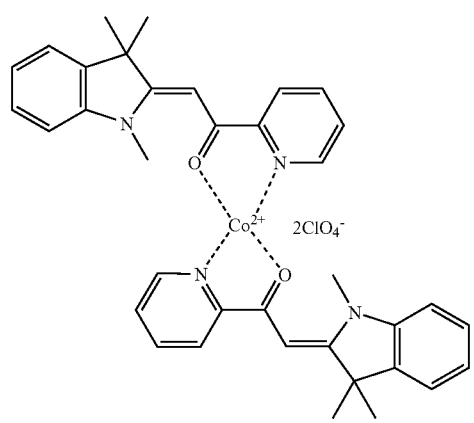
Compound No. 55
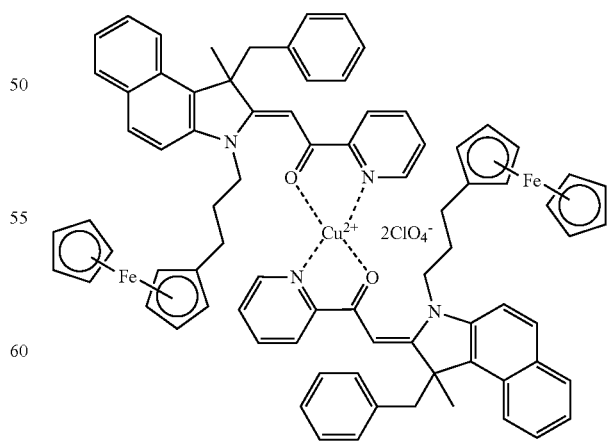

Compound No. 56
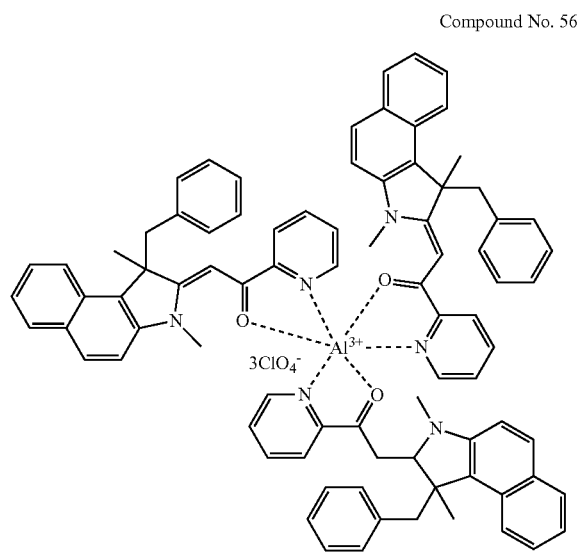
Compound No. 60
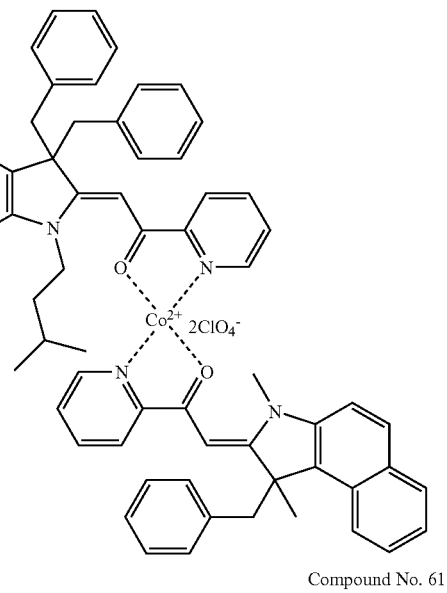
Other specific examples of the metal complex represented by the general formula (VI) include the following compound Nos. 59 to 64:
[Formula 18]
Compound No. 61
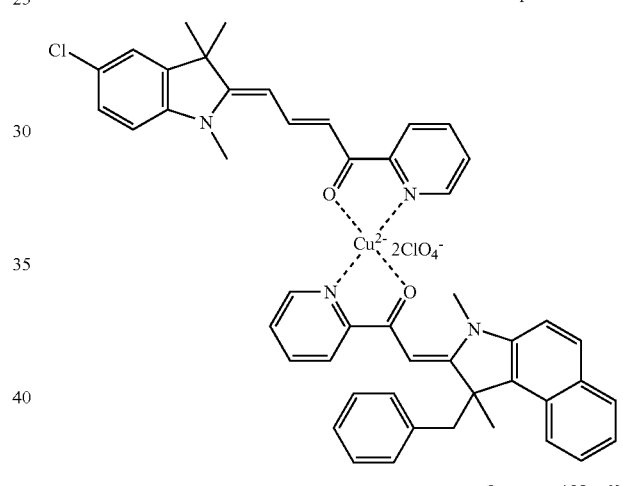
Compound No. 59
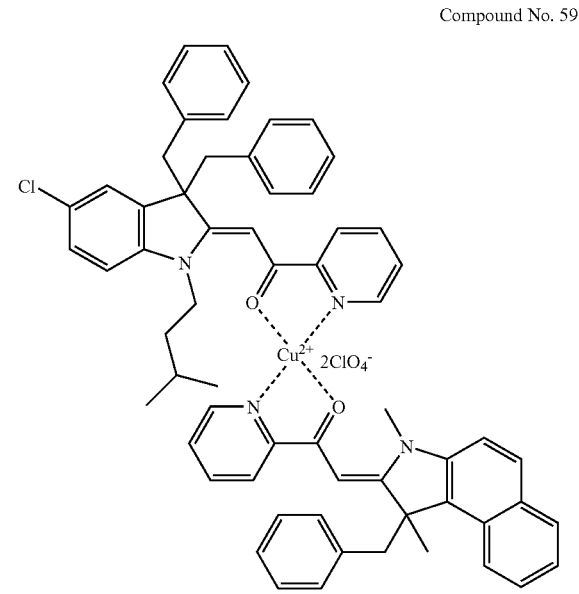
Compound No. 62
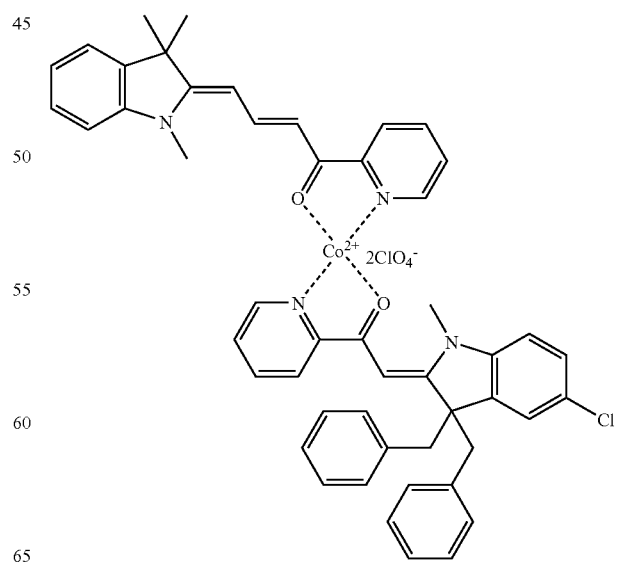

-continued

Compound No. 63

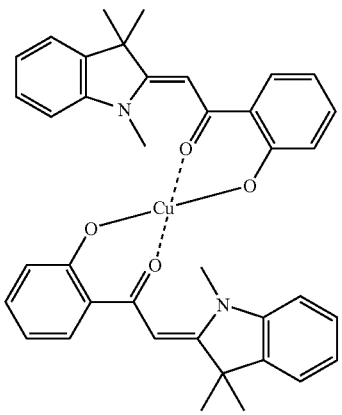

Compound No. 64

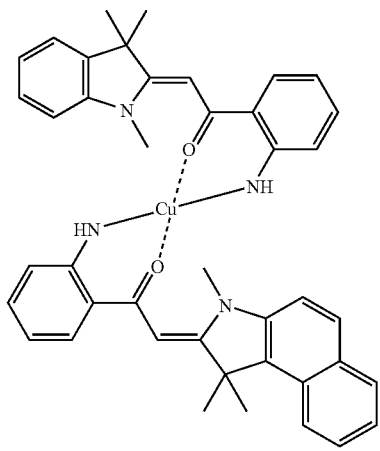

The metal complex using as a ligand the chalcone type compound represented by any of the general formula (I) to (V) of the present invention is not particularly restricted by the method of manufacture. For example, it may be synthesized by a chelating reaction between the chalcone type compound which is the corresponding ligand and a metal compound.

The metal salt compound used in the above-mentioned chelating reaction includes, for example, an inorganic metal salt such as a metal halide, hydroxide, sulfate, nitrate salts, and the like; an organic metal salt such as an acetate salt and the like; a metal lower alkoxide such as methoxide, ethoxide, isopropoxide, and the like; a chelate complex such as an acetylacetonate, EDTA salts, and the like. Further, in the chelating reaction, there may be used as a reactant, as necessary, basic compounds such as sodium hydroxide, lithium hydroxide, sodium methoxide, sodium hydride, sodium amide, lithium amide, an organic amine compound, and the like.

The optical recording material of the present invention comprises at least one kind of chalcone type compound represented by any of the general formulae (I) to (V) or a metal complex using these compounds as ligands, and is used as these compounds or as a mixture of these compounds with the solvent or various compounds, which will be described later. There is no particular restriction on the method of forming an optical recording layer of the optical recording medium using such an optical recording material of the present invention. Generally, the above-mentioned chalcone type compound or the metal complex and, if necessary, various compounds described later are dissolved in an organic solvent to prepare the optical recording material as a solution, the organic solvent including a lower alcohol such as methanol, ethanol, and the like; an ether alcohol such as methyl cellosolve, ethyl cellosolve, butyl cellosolve, butyl diglycol, and the like; a ketone such as acetone, methyl ethyl ketone, methyl isobutyl ketone, cyclohexanone, diacetone alcohol, and the like; an ester such as ethyl acetate, butyl acetate, methoxyethyl acetate, and the like; an acrylic acid ester such as ethyl acrylate, butyl acrylate, and the like; fluorinated alcohols such as 2,2,3,3-tetrafluoropropanol and the like; a hydrocarbon such as benzene, toluene, xylene, and the like; a chlorinated hydrocarbon such as methylene dichloride, dichloroethane, chloroform, and the like. The optical recording material is coated on a substrate by a wet coating method including spin coating, spraying, dipping, and the like. Other methods such as vapor deposition, sputtering, and the like may also be mentioned. When the organic solvent is used, its amount is preferably such that the content of the chalcone type compound or the metal complex becomes 0.1 to 10% by mass of the optical recording material of the present invention.

The optical recording layer is formed as a thin film and its suitable thickness is usually 0.001 to 10 μm, preferably in a range of 0.01 to 5 μm.

Further, the above-mentioned optical recording layer is formed in such a way that the content of the chalcone type compound or the metal complex containing these compounds as ligands is preferably 10 to 100% by weight, especially 50 to 100% by mass, of the optical recording layer. In order to form an optical recording layer of such a content of the chalcone type compound or the metal complex, the optical recording material of the present invention preferably contains the chalcone type compound represented by any of the general formula (I) to (V) of the present invention or the metal complex containing these as ligands in an amount of 50 to 1000 by mass, based on the solid content of the optical recording material of the invention.

In addition to the chalcone type compound represented by the general formulae (I) to (V) or the metal complex of these compounds, the optical recording layer may contain, as necessary, a compound used for an optical recording layer such as a cyanine compound, azo compound, phthalocyanine compound, squarylium compound, and the like; a resin such as polyethylene, polyester, polystyrene, polycarbonate, and the like; a surfactant; an antistatic agent; a lubricating agent; a fire retardant; a radical trapping agent such as a hindered amine and the like; a pit formation accelerator such as a ferrocene derivative and the like; a dispersant; an antioxidant; a crosslinking agent; a light resistance improver; and the like. Further, the optical recording layer may contain, as a quencher for the singlet oxygen and the like, an aromatic nitroso compound, aminium compound, iminium compound, bisiminium compound, transition metal dithiol chelate compound, and the like.

These various compounds are used preferably in a total amount ranging from 0 to 50% by mass in the optical recording layer. For that purpose, these other compounds are contained in the optical recording material of the present invention preferably in an amount of 0 to 50% by mass based on the solid content.

There is no particular restriction on the material used as the substrate on which such an optical recording layer is formed, provided that it is essentially transparent to the writing (recording) light and reading (reproducing) light, examples including resins such as poly(methyl methacrylate), poly(ethylene terephthalate), polycarbonate, and the like; glass and the like. Further, its shape is optionally selected corresponding to the application, from a tape, drum, belt, disc, and the like.

Further, there may be formed on the optical recording layer a reflection film by means of a vapor deposition or sputtering method using gold, silver, aluminum, copper, and the like. Dielectric layers may be formed on one or both sides by a sputtering method, or protection layers may also be formed on one or both sides using an acrylic resin, an ultraviolet curing resin, and the like.

The optical recording material of the present invention is suitable for an optical recording medium in which a semiconductor laser is used for recording and reproducing, especially suitable for publicly known single-, double-, or multi-layer optical discs such as CD-R, DVD±R, HD-DVD-R, BD-R, and the like, which are of a high-speed recording type.

As mentioned above, the novel chalcone type compound of the present invention represented by the general formula (III) may be used preferably as an optical recording material. In addition, it may also be used for an optical filter and the like.

In addition, the novel metal complex of the present invention represented by the general formula (VI) may be used preferably as an optical recording material. In addition, it may also be used for an optical filter and the like.

EXAMPLES

Hereafter, the present invention will be described in more detail in terms of Examples, Comparative Examples, and Evaluation Examples. However, the present invention will not be limited in any way by the following Examples and the like.

The following Manufacturing Examples 1 to 10 show examples of manufacture of chalcone type compounds of the present invention, compound Nos. 1 to 8, No. 22, and No. 30. The following manufacturing examples 11 to 25 show examples of manufacture of metal complexes of the present invention, compound Nos. 43 to 57 using the compound Nos. 1 to 6 as ligands.

Further, the following Examples 1 to 19 show examples of preparation of optical recording materials of the present invention comprising compound Nos. 1 to 8 obtained in Manufacturing Examples 1 to 8 or compound Nos. 46 to 56 obtained in Manufacturing Examples 14 to 24. The Examples also show the manufacturing examples of the optical recording media of the present invention Nos. 1 to 19 using the optical recording materials.

The following Comparative Example 1 shows an example of preparation of the comparative optical recording material using a chalcone type compound having a different structure from the compound of the present invention and also shows an example of manufacture of the comparative optical recording medium No. 1 using the comparative optical recording material.

In the following Evaluation Examples 1-1 to 1-19 and Comparative Evaluation Example 1-1, recordability by a short wavelength laser light of optical recording media Nos. 1 to 19 obtained in Examples 1 to 19 and a comparative optical recording medium No. 1 obtained in Comparative Example 1 was evaluated by measurement of UV absorption spectrum. The results are shown in [Table 7].

In the following Evaluation Examples 2-1 to 2-9 and Comparative Evaluation Example 2-1, light resistance of the optical recording media Nos. 9 to 11, 13 and 15 to 19 obtained in Examples 9 to 11, 13, and 15 to 19 as well as the comparative optical recording medium No. 1 obtained in the Comparative Example 1 was evaluated by measuring the residual rate of absorbance at the maximum absorption wavelength (λmax) in the UV absorption spectrum. The results are shown in [Table 8].

Manufacturing Examples 1 to 10

Manufacture of Chalcone Type Compound

Using the synthetic methods 1 to 3 described below, the compound Nos. 1 to 8, No. 22, and No. 30 were synthesized. The yields and analytical results (λmax, melting point, decomposition point, IR absorption spectrum, $^1$H-NMR) are shown in [Table 1] to [Table 3].

It is noted that, in [Table I], the decomposition point refers to the temperature in the differential thermal analysis performed at a heating rate of 10° C./min., whereat the mass of the sample begins to decrease.

(Synthetic Method 1) Synthesis of Compound Nos. 1 to 8

To a reaction vessel were charged 30 mmol of a quaternary salt of indolenine, 33 mmol of picolinic acid chloride hydrochloride, and 47 g of 1,2-dichloroethane. To this was dropwise added 90 mmol of triethylamine at 0° C. and the reaction mixture was stirred at room temperature for 17 hrs. After dropwise addition of 15 ml of 1 N hydrochloric acid, 50% aqueous potassium hydroxide was added until the solution turned basic and the oil phase was separated. After removal of the solvent by distillation, the residue was purified by column chromatography (silica gel; n-hexane:ethyl acetate=3:1) and recrystallized from methanol to obtain the desired chalcone type compound.

(Synthetic Method 2) Synthesis of Compound No. 22

To a reaction vessel were charged 30 mmol of indolenine aldehyde, 33 mmol of methyl pyridyl ketone, and 47 g of ethanol. To this was dropwise added 90 mmol of triethylamine at 0° C. and the reaction mixture was stirred at 100° C. for 17 hrs. After dropwise addition of 15 ml of 1 N hydrochloric acid, 50% aqueous potassium hydroxide was added until the solution became basic and the oil phase was separated. After removal of the solvent by distillation, the residue was purified by column chromatography (silica gel; n-hexane:ethyl acetate=3:1) and recrystallized from methanol to obtain the desired chalcone type compound.

(Synthetic Method 3) Synthesis of Compound No. 30

<Step 1> Manufacture of Quaternary Salt

To a reaction flask purged with nitrogen were added 0.500 mol of 2-naphthylhydrazine and 275 g of ethanol. To this was dropwise added, under a nitrogen flow, 0.600 mol of 4-phenylbutan-2-one at 55° C. After stirring for 30 minutes, 0.5 mol of sulfuric acid was dropwise added, paying attention to heat evolution, and the reaction mixture was refluxed for 1 hr. After cooling, 1000 g each of toluene and water were added and, successively, 50% aqueous sodium hydroxide was added until the pH of the mixture became 8 or higher. The oil phase was separated, washed with 500 g each of water 3 times, and, the water and the solvent were removed. The residue was recrystallized from 137 g of toluene and dried to give crude crystals. The crude crystals obtained were placed in an autoclave, to which were added 0.200 mol of methyl iodide and 20 g of methanol, and the reaction was carried out at 100° C. for 15 hrs. After removal of the solvent, the residue was recrystallized from a mixed solvent of ethyl acetate (100 g)/methanol (6.00 g) and dried to obtain the desired crude crystals.

<Step 2> Manufacture of Compound No. 30

To a reaction flask purged with nitrogen, 0.02 mol of the quaternary salt obtained in Step 1, 0.04 mol of pyridine, and 0.2 mol of an acid anhydride were added and the reaction mixture was stirred at 50° C. for 1 to 4 hrs. To this was added 20 g each of chloroform and water. The oil phase was separated, the solvent was removed, and the residue was recrystallized from a mixed solvent of ethyl acetate/n-hexane to obtain the desired chalcone type compound.

TABLE 1

| | Chalcone type compound | Yield (%) | Melting point (° C.) | Decomposition point (° C.) |
|---|---|---|---|---|
| Manufacturing Example 1 | Compound No. 1 | 74 | — | 243 |
| Manufacturing Example 2 | Compound No. 2 | 43 | 130 | 252 |
| Manufacturing Example 3 | Compound No. 3 | 61 | 99 | 227 |
| Manufacturing Example 4 | Compound No. 4 | 66 | 186 | 291 |
| Manufacturing Example 5 | Compound No. 5 | 34 | 140 | 260 |
| Manufacturing Example 6 | Compound No. 6 | 49 | — | 262 |
| Manufacturing Example 7 | Compound No. 7 | 23 | — | 226 |
| Manufacturing Example 8 | Compound No. 8 | 8 | 138 | 287 |
| Manufacturing Example 9 | Compound No. 22 | 24 | 146 | 201 |
| Manufacturing Example 10 | Compound No. 30 | 22 | 152 | 148 |

TABLE 2

| | Chalcone type compound | IR absorption spectrum (cm-1) |
|---|---|---|
| Manufacturing Example 1 | Compound No. 1 | 3053, 1628, 1589, 1538, 1513, 1460, 1442, 1425, 1365, 1324, 1215, 1143, 1052. |
| Manufacturing Example 2 | Compound No. 2 | 2957, 1622, 1564, 1526, 1474, 1456, 1426, 1364, 1265, 1203, 1142, 1086. |
| Manufacturing Example 3 | Compound No. 3 | 3054, 2958, 1626, 1533, 1487, 1464, 1430, 1381, 1353, 1289, 1248. |
| Manufacturing Example 4 | Compound No. 4 | 2966, 1625, 1568, 1539, 1515, 1475, 1441, 1428, 1366, 1325, 1263, 1215. |
| Manufacturing Example 5 | Compound No. 5 | 3056, 1744, 1626, 1591, 1545, 1500, 1462, 1440, 1428, 1374, 1355, 1324, 1219. |
| Manufacturing Example 6 | Compound No. 6 | 3056, 2933, 1735, 1629, 1582, 1565, 1536, 1513, 1462, 1442, 1429, 1394, 1366. |
| Manufacturing Example 7 | Compound No. 7 | 2933, 1628, 1588, 1568, 1541, 1516, 1472, 1366, 1328, 1237. |
| Manufacturing Example 8 | Compound No. 8 | 2933, 1708, 1611, 1583, 1540, 1513, 1463, 1432, 1368, 1349, 1320, 1215. |
| Manufacturing Example 9 | Compound No. 22 | 2965, 1699, 1637, 1612, 1581, 1527, 1488, 1458, 1384, 1344, 1290, 1206, 1189, 1130, 1117, 1080. |
| Manufacturing Example 10 | Compound No. 30 | 2919, 1726, 1628, 1532, 1511, 1371, 1328, 1230, 1138, 1057. |

TABLE 3

| | Chalcone type compound | $^1$H-NMR (ppm) |
|---|---|---|
| Manufacturing Example 1 | Compound No. 1 | (solvent CDCl3): 8.68-6.50 (m, 16H), 5.02 (d, 1H), 3.64 (d, 1H), 3.14 (s, 3H), 2.30 (s, 3H) |
| Manufacturing Example 2 | Compound No. 2 | (solvent CDCl3): 8.69-6.27 (m, 18H), 4.68 (t, 2H), 3.29 (d, 4H), 1.31 (m, 1H), 0.81 (d, 6H), 0.75 (m, 2H) |
| Manufacturing Example 3 | Compound No. 3 | (solvent CDCl3): 8.62 (d, 1H), 8.16 (d, 1H), 7.81 (t, 1H), 7.35 (t, 1H), 7.23-7.20 (m, 2H), 7.07 (s. 1H), 7.02 (t 1H), 6.79 (d, 1H), 3.83 (t, 2H), 1.87 (s, 6H), 1.80 (m, 2H), 1.07 (d, 2H) |
| Manufacturing Example 4 | Compound No. 4 | (solvent DMSO-d6): 8.67 (d, 1H), 8.08 (t, 2H), 8.02-7.89 (m, 3H), 7.56-7.50 (m, 3H), 7.34 (t, 1H), 6.99 (s, 1H), 3.40 (s, 3H), 2.04-2.02 (m, 6H) |
| Manufacturing Example 5 | Compound No. 5 | (solvent DMSO-d6): 8.67 (d, 1H), 8.13 (d, 1H), 8.08 (d, 1H), 7.98-7.89 (m, 3H), 7.56-7.49 (m, 3H), 7.36 (t, 1H), 7.06 (s, 1H), 5.02 (d, 1H), 4.62-4.52 (m, 2H), 4.02 (d, 1H), 3.70 (s, 3H), 2.06 (s, 3H), 1.15 (t, 1H) |
| Manufacturing Example 6 | Compound No. 6 | (solvent CDCl3): 8.68 (d, 1H), 8.29 (t, 2H), 7.89-7.86 (m, 2H), 7.73 (d, 1H), 7.62 (t, 1H), 7.40 (t, 2H), 7.14 (s, 1H), 6.89-6.88 (m, 2H), 6.77 (d, 2H), 6.49 (d, 2H), 5.05 (d, 1H), 4.07-4.02 (m, 9H), 3.69-3.57 (m, 3H), 2.30 (s, 3H), 2.26 (t, 2H), 1.37-1.29 (m, 4H) |

TABLE 3-continued

| | Chalcone type compound | $^1$H-NMR (ppm) |
|---|---|---|
| Manufacturing Example 7 | Compound No. 7 | (solvent DMSO-d6): 8.30 (d, 1H), 7.92 (d, 1H), 7.85 (d, 1H), 7.80 (d, 1H), 7.61 (t, 1H), 7.38 (t, 1H), 7.26 (d, 1H), 7.22 (d, 1H), 6.87-6.76 (m, 4H), 6.41 (d, 2H), 6.07 (s, 1H), 4.80 (d, 1H), 3.58 (d, 1H), 3.12 (s, 3H), 2.13 (s, 3H) |
| Manufacturing Example 8 | Compound No. 8 | (solvent DMSO-d6): 8.29 (d, 1H), 7.92-7.90 (m, 2H), 7.81-7.78 (m, 2H), 7.61 (t, 1H), 7.38 (t, 1H), 7.22-7.18 (m, 2H), 6.87-6.76 (m, 3H), 6.41 (d, 2H), 6.14 (s, 1H), 4.80 (d, 1H), 3.59 (d, 1H), 3.10 (s, 3H), 2.13 (s, 3H) |
| Manufacturing Example 9 | Compound No. 22 | (solvent CDCl3): 8.69-6.74 (m, 10H), 5.72 (d, 1H), 3.23 (s, 3H), 1.67 (s, 6H) |
| Manufacturing Example 10 | Compound No. 30 | (solvent CDCl3): 12.9 (s, 1H), 8.33-6.56 (m, 15H), 4.82 (d, 1H), 3.54 (d, 1H), 3.34 (s, 1H), 3.00 (s, 3H), 2.12 (s, 3H), |

Manufacturing Example Nos. 11 to 25

Manufacture of Compound Nos. 43 to 57

(Metal Complexes)

Using the synthetic method shown below, compound Nos. 43 to 57 were synthesized. The yields and analytical results (decomposition point, IR absorption spectrum, elemental analysis) of the compounds obtained are shown in [Table 4] to [Table 6].

It is noted that, in [Table 4], the decomposition point refers to the temperature in the differential thermal analysis performed at a heating rate of 10° C./min, whereat the mass of the sample begins to decrease.

(Synthetic Method) Synthesis of Compound Nos. 43 to 57

To a reaction flask were added 4 mmol of any of compounds Nos. 1 to 6 or No. 22 obtained in Manufacturing Examples 1 to 6 or Manufacturing Example 9, 4 mmol of metal perchlorate hydrate or metal chloride, and 30 g of methanol, and the reaction mixture was stirred at 60° C. for 3 hrs. The precipitate was collected by filtration and was washed with methanol to obtain the desired metal complex.

TABLE 4

| | Metal complex | Yield (%) | Decomposition point (° C.) |
|---|---|---|---|
| Manufacturing Example 11 | Compound No. 43 | 28 | 227 |
| Manufacturing Example 12 | Compound No. 44 | 75 | 211 |
| Manufacturing Example 13 | Compound No. 45 | 84 | 292 |
| Manufacturing Example 14 | Compound No. 46 | 87 | 250 |
| Manufacturing Example 15 | Compound No. 47 | 85 | 285 |
| Manufacturing Example 16 | Compound No. 48 | 88 | 218 |
| Manufacturing Example 17 | Compound No. 49 | 51 | 312 |
| Manufacturing Example 18 | Compound No. 50 | 94 | 255 |
| Manufacturing Example 19 | Compound No. 51 | 73 | 270 |
| Manufacturing Example 20 | Compound No. 52 | 98 | 286 |
| Manufacturing Example 21 | Compound No. 53 | 77 | 247 |
| Manufacturing Example 22 | Compound No. 54 | 78 | 231 |
| Manufacturing Example 23 | Compound No. 55 | 86 | 207 |
| Manufacturing Example 24 | Compound No. 56 | 75 | 248 |
| Manufacturing Example 25 | Compound No. 57 | 43 | 250 |

TABLE 5

| | Metal complex | IR absorption spectrum (cm−1) |
|---|---|---|
| Manufacturing Example 11 | Compound No. 43 | 3026, 1540, 1518, 1462, 1374, 1244, 1157, 1052. |
| Manufacturing Example 12 | Compound No. 44 | 3028, 1541, 1518, 1468, 1369, 1247, 1156, 1055. |
| Manufacturing Example 13 | Compound No. 45 | 3036, 1528, 1469, 1435, 1401, 1327, 1267, 1144, 1098. |
| Manufacturing Example 14 | Compound No. 46 | 3027, 1546, 1518, 1470, 1364, 1249, 1102. |
| Manufacturing Example 15 | Compound No. 47 | 3438, 1533, 1516, 1464, 1388, 1371, 1245, 1122, 1026. |
| Manufacturing Example 16 | Compound No. 48 | 3027, 1533, 1515, 1461, 1383, 1361, 1241, 1154, 1101, 1023. |
| Manufacturing Example 17 | Compound No. 49 | 3030, 1523, 1469, 1456, 1434, 1404, 1266, 1142, 1123, 1024. |
| Manufacturing Example 18 | Compound No. 50 | 3074, 2975, 1628, 1532, 1515, 1462, 1386, 1291, 1245. |
| Manufacturing Example 19 | Compound No. 51 | 3539, 2959, 1522, 1461, 1403, 1368, 1345, 1293, 1270, 1241. |

TABLE 5-continued

| | Metal complex | IR absorption spectrum (cm−1) |
|---|---|---|
| Manufacturing Example 20 | Compound No. 52 | 3488, 1531, 1515, 1465, 1366, 1295, 1270, 1242, 1210. |
| Manufacturing Example 21 | Compound No. 53 | 3465, 3031, 1550, 1519, 1469, 1384, 1370, 1287, 1253, 1224. |
| Manufacturing Example 22 | Compound No. 54 | 3030, 2936, 1547, 1519, 1467, 1384, 1361, 1283, 1252, 1231. |
| Manufacturing Example 23 | Compound No. 55 | 3524, 3086, 2934, 1542, 1517, 1465, 1395, 1361, 1281, 1229. |
| Manufacturing Example 24 | Compound No. 56 | 3525, 3059, 1560, 1471, 1380, 1359, 1280, 1253, 1228. |
| Manufacturing Example 25 | Compound No. 57 | 2970, 1584, 1568, 1482, 1451, 1375, 1289, 1252, 1202, 1158, 1100, 1018 |

TABLE 6

| | Metal complex | Elemental analysis: Cu/C/H/N (% by mass) |
|---|---|---|
| Manufacturing Example 14 | Compound No. 46 | 5.93/62.78/4.52/5.23 (Theoretical value: 5.93/62.77/4.48/5.23) |

Examples 1 to 19

Preparation of optical recording materials and manufacture of optical recording media The chalcone type compounds obtained in the Manufacturing Examples 1 to 8 and the metal complexes obtained in the Manufacturing Examples 14 to 24 were each dissolved in 2,2,3,3-tetrafluoropropanol at concentrations of 1.0% by mass to obtain the optical recording materials of Examples 1 to 19 as 2,2,3,3-tetrafluoropropanol solutions. The optical recording material was spin coated on a polycarbonate disc substrate of 12 cm diameter, to form a 100 nm thick optical recording layer and obtain the respective optical recording media, the disc having been provided with a foundation layer (0.01 pm) by coating a titanium chelate compound (T-50: manufactured by Nippon Soda Co., Ltd.), followed by hydrolysis.

Comparative Examples 1

Except that the following comparative compound No. 1 was used as the chalcone type compound, the comparative optical recording material was prepared in a similar manner as in Examples 1 to 19 and, using the comparative optical recording material, the comparative optical recording medium was obtained:

[Formula 19]

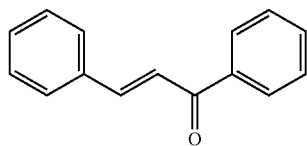

Comparative compound No. 1

Evaluation Example 1

UV absorption spectra were measured of the optical recording media of Examples 1 to 19 and the comparative optical recording medium of Comparative Example 1. The results are shown in [Table 7]. It is noted that the absorbance ratio at 405 nm in [Table 7] refers to the relative value of the absorbance at 405 nm against the absorbance at λmax in the UV spectrum.

TABLE 7

| Optical recording medium | Compound | λmax (nm) | Absorbance ratio at 405 nm (%) |
|---|---|---|---|
| Evaluation Example 1-1 | NO. 1 | NO. 1 | 425.0 | 78.1 |
| Evaluation Example 1-2 | NO. 2 | NO. 2 | 408.0 | 99.4 |
| Evaluation Example 1-3 | NO. 3 | NO. 3 | 397.0 | 95.8 |
| Evaluation Example 1-4 | NO. 4 | NO. 4 | 421.0 | 86.6 |
| Evaluation Example 1-5 | NO. 5 | NO. 5 | 423.0 | 83.0 |
| Evaluation Example 1-6 | NO. 6 | NO. 6 | 431.0 | 67.7 |
| Evaluation Example 1-7 | NO. 7 | NO. 7 | 420.0 | 88.6 |
| Evaluation Example 1-8 | NO. 8 | NO. 8 | 424.0 | 80.9 |
| Evaluation Example 1-9 | NO. 9 | NO. 46 | 473.0 | 36.1 |
| Evaluation Example 1-10 | NO. 10 | NO. 47 | 456.0 | 41.9 |
| Evaluation Example 1-11 | NO. 11 | NO. 48 | 468.0 | 41.5 |
| Evaluation Example 1-12 | NO. 12 | NO. 49 | 442.0 | 59.2 |
| Evaluation Example 1-13 | NO. 13 | NO. 50 | 468.0 | 40.4 |
| Evaluation Example 1-14 | NO. 14 | NO. 51 | 443.0 | 67.6 |
| Evaluation Example 1-15 | NO. 15 | NO. 52 | 462.0 | 49.5 |
| Evaluation Example 1-16 | NO. 16 | NO. 53 | 472.0 | 37.4 |
| Evaluation Example 1-17 | NO. 17 | NO. 54 | 464.0 | 42.2 |
| Evaluation Example 1-18 | NO. 18 | NO. 55 | 478.0 | 30.5 |
| Evaluation Example 1-19 | NO. 19 | NO. 56 | 464.0 | 53.9 |

As the optical recording media typified by optical discs, preferable are those having adequate absorptions near the wavelength of laser light, namely those with the absorbance ratio relative to $\lambda_{max}$ of 5 to 70%, more preferably 10 to 60%. When the absorbance ratio is 5%, the sensitivity and degree of modulation are not enough. When the absorbance ratio is 70% or higher, it is possible that an adequate degree of reflection is not obtained or that deterioration by reproducing light occurs.

It was confirmed that the optical recording media, comprising the optical recording layer formed of the optical recording material of the present invention have, the absorbance ratio relative to λmax of 30 to 60% and are suitable as an optical recording material for the optical recording media which utilize laser light of 405 nm.

Evaluation Example 2

Evaluation of Light Resistance

The light resistance was evaluated of the optical recording media of Examples 9 to 11, 13, 15 to 19, and Comparative Example 1. As for evaluation, each of the optical recording media was irradiated by light of 55,000 lux for 100 hrs., whereafter the residual rate of absorbance in the UV absorption spectrum at λmax before the irradiation was measured. The results are shown in [Table 8].

TABLE 8

| | Optical recording medium | Compound | Residual rate of absorbance (%) |
|---|---|---|---|
| Evaluation Example 2-1 | NO. 9 | NO. 46 | 86.6 |
| Evaluation Example 2-2 | NO. 10 | NO. 47 | 88.4 |
| Evaluation Example 2-3 | NO. 11 | NO. 48 | 77.9 |
| Evaluation Example 2-4 | NO. 13 | NO. 50 | 57.5 |
| Evaluation Example 2-5 | NO. 15 | NO. 52 | 90.9 |
| Evaluation Example 2-6 | NO. 16 | NO. 53 | 82.3 |
| Evaluation Example 2-7 | NO. 17 | NO. 54 | 76.6 |
| Evaluation Example 2-8 | NO. 18 | NO. 55 | 92.8 |
| Evaluation Example 2-9 | NO. 19 | NO. 56 | 26.6 |
| Comparative Evaluation Example 2-1 | Comparative optical recording medium No. 1 | Comparative compound No. 1 | 0 |

As is clear from [Table 8], the optical recording material of the present invention has a high light resistance and is suitable for formation of an optical recording layer of the optical recording medium.

Industrial Applicability

The present invention provides a chalcone type compound, a metal complex using the compound as a ligand, and an optical recording material comprising these, which are suitable for formation of an optical recording layer of an optical recording medium for short wavelength recording light.

The invention claimed is:

1. An optical recording material comprising at least one chalcone compound represented by general formulas (V)

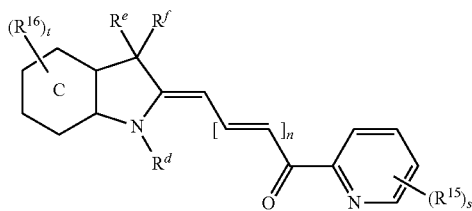

(V)

wherein,
n is 0 or 1;
ring C represents a naphthalene ring ;
t represents an integer from 0 to 6;
each $R^{16}$ is the same or different and represents an alkyl group having 1 to 8 carbon atoms which may optionally be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;
$R^d$, $R^e$, and $R^f$ each independently represents a hydrogen atom, an alkyl group having 1 to 8 carbon atoms, an alkenyl group having 2 to 8 carbon atoms, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;
s represents an integer from 0 to 4 ;
each $R^{15}$ is the same or different and represents an alkyl group having 1 to 8 carbon atoms which may optionally be interrupted by —O—, —CO—, —OCO—, or —COO—, and aryl group having 6 to 30 carbon atoms, an arylalkyl group having 7 to 30 carbons atoms, a metallocenyl group having 10 to 30 carbon atoms, a halogen atom, a hydroxyl group, a nitro group, a cyano group or a heterocyclic group having 2 to 30 carbons atoms; and
each of said alkyl group having 1 to 8 carbon atoms, said aryl group having 6 to 30 carbon atoms, said arylalkyl group having 7 to 30 carbon atoms, said metallocenyl group having 10 to 30 carbon atoms, and said heterocyclic group having 2 to 30 carbon atoms of $R^{15}$, $R^{16}$, $R^d$, $R^e$, and $R^f$ may optionally have a substituent.

2. The optical recording material according to claim 1, wherein the at least one chalcone compound is present in the amount of 50% to 100% by mass based on the solid content of the optical recording material.

3. An optical recording medium, comprising an optical recording layer disposed on a substrate, the optical recording layer formed of an optical recording material comprising at least one chalcone compound represented by general formula (V)

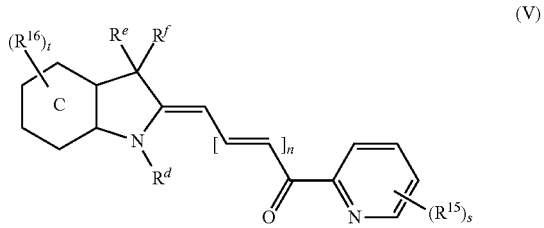

(V)

wherein,
n is 0 or 1;
ring C represents a benzene or naphthalene ring;
t represents an integer from 0 to 6;
each $R^{16}$ is the same or different and represents an alkyl group having 1 to 8 to carbon atoms which may optionally be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;

$R^d$, $R^e$, and $R^f$ each independently represent a hydrogen atom, an alkyl group having 1 to 8 carbon atoms, an alkenyl group having 2 to 8 carbon atoms, an aryl group having 6 to 30 carbon atoms, an arylalkyl group having 7 to 30 carbon atoms, a metallocenyl group having 10 to 30 carbon atoms, a halogen atoms, a hydroxyl group, a nitro group, a cyano group, or a heterocyclic group having 2 to 30 carbon atoms;

s represents an integer from 0 to 4;

each $R^{15}$ is the same or different and represents an alkyl group having 1 to 8 carbon atoms which may optionally be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms; and each of said alkyl group having 1 to 8 carbon atoms, said aryl group having 6 to 30 carbon atoms, said arylalkyl group having 7 to 30 carbon atoms, said metallocenyl group having 10 to 30 carbon atoms, and said heterocyclic group having 2 to 30 carbon atoms of $R^{15}$, $R^{16}$, $R^d$, $R^e$, and $R^f$ may optionally have a substituent.

4. The optical recording medium according to claim 3, wherein the at least one chalcone compound is present in the amount of 50% to 100% by mass based on the solid content of the optical recording material.

5. A metal complex represented by general formula (VI):

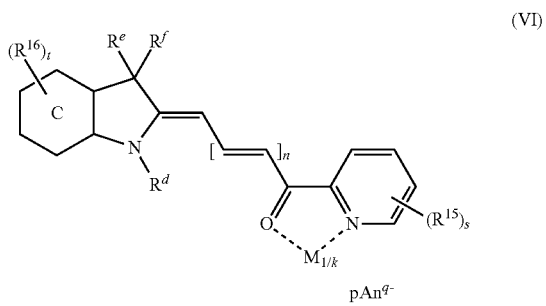

wherein
ring C represents a benzene or naphthalene ring;
t represents an integer from 0 to 6;
each $R^{16}$ is the same or different and represents an alkyl group having 1 to 8 carbon atoms which may optionally be interrupted by —O—, —CO—, —OCO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;

$R^d$, $R^e$, and $R^f$ each independently represent a hydrogen atom, an alkyl group having 1 to 8 carbon atoms, an alkenyl group having 2 to 8 carbon atoms, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;

s represents an integer from 0 to 4;

each $R^{15}$ is the same or different and represents an alkyl group having 1 to 8 carbon atoms which may optionally be interrupted by —O—, —CO—, —COO—, or —COO—, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;

M represents a metal atom selected from the group consisting of the elements of the periodic table Groups 2, 8, 9, 10, 11, 12, and 13;

$M_{1/k}$ represents a structure where k ligands that are the same coordinate to metal M;

k is an integer from 2 to 4;

$An^{q-}$ represents a q-valent anion;

q is 1 or 2; and p represents a coefficient to keep the charge neutral.

6. An optical recording material comprising a metal complex having a chalcone compound as a ligand, the metal complex being represented by general formula (VI):

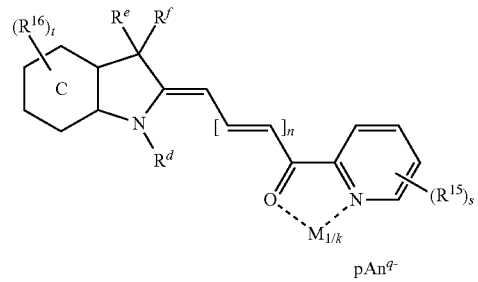

wherein
n is 0 or 1;
ring C represents a benzene or naphthalene ring;
each $R^{16}$ is the same or different and represents an alkyl group having 1 to 8 carbon atoms which may optionally be interrupted by —O—, —CO—, —OCO—, or —COO—, and aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;
t represents an integer from 0 to 6;
$R^d$, $R^e$, and $R^f$ each independently represents a hydrogen atom, an alkyl group having 1 to 8 carbon atoms, an alkenyl group having 2 to 8 carbon atoms, an aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;
each of said alkyl group having 1 to 8 carbon atoms, said aryl group having 6 to 30 carbon atoms, said arylalkyl group having 7 to 30 carbon atoms, said metallocenyl group having 10 to 30 carbon atoms, and said heterocyclic group having 2 to 30 carbon atoms of $R^{16}$, $R^d$, $R^e$, and $R^f$ optionally has a substituent;
s represents an integer from 0 to 4;
each $R^{15}$ is the same or different and represents an alkyl group having 1 to 8 carbon atoms which may optionally be interrupted by —O—, —CO—, —OCO—, or —COO—, and aryl group having 6 to 30 carbon atoms, an arylalkyl group having 7 to 30 carbon atoms, a metallocenyl group having 10 to 30 carbon atoms, a halogen atom, a hydroxyl group, a nitro group, a cyano group, or a heterocyclic group having 2 to 30 carbon atoms;

M represents a metal atom selected from the group consisting of the elements of the periodic table Groups 2, 8, 9, 10, 11, 12, and 13;

$M_{1/k}$ represents a structure where k ligand that are the same coordinate to metal M;

k is an integer from 2 to 4;

$An^{q-}$ represents a q-valent anion ;

q is 1 or 2; and p represents a coefficient to keep the charge neutral.

7. The optical recording material according to claim 6, wherein the metal complex represented by general formula (VI) is present in the amount of 50% to 100% by mass based on the solid content of the optical recording material.

8. The optical recording material according to claim 6, wherein the metal complex comprises a metal selected from the group consisting of: copper, nickel, cobalt, iron, and aluminum.

9. An optical recording medium, comprising an optical recording layer disposed on a substrate, the optical recording layer formed of the optical recording material according to claim 6.

10. An optical recording medium, comprising an optical recording layer disposed on a substrate, the optical recording layer formed of the optical recording material according to claim 7.

11. An optical recording medium comprising an optical recording layer disposed on a substrate, the optical recording layer formed of the optical recording material according to claim 8.

12. An optical recording medium, comprising an optical recording layer disposed on a substrate, the optical recording layer formed of an optical recording material comprising a metal complex having a chalcone compound as a ligand, the chalcone compound being represented by general formula (I):

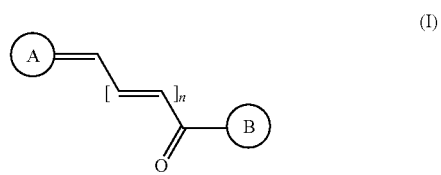

wherein,
ring A represents a 5- or 6-membered heterocyclic ring;
ring B represents a 5- or 6-membered heterocyclic ring, an aromatic ring, or a metallocene structure;
the 5- or 6-membered heterocyclic rings and aromatic rings may optionally be condensed with other heterocyclic and aromatic rings or may optionally be substituted; and
n is 0 or 1.

13. The optical recording medium according to claim 12, wherein the metal complex comprises a metal selected from the group consisting of: cooper, nickel, cobalt, iron, and aluminum.

* * * * *